United States Patent [19]

Lombardo et al.

[11] 4,317,520

[45] Mar. 2, 1982

[54] SERVO SYSTEM TO CONTROL THE SPATIAL POSITION OF DROPLET FORMATION OF A FLUID JET IN A CELL SORTING APPARATUS

[75] Inventors: Igino Lombardo, Sharon; Richard A. Dussault, Attleboro, both of Mass.

[73] Assignee: Ortho Diagnostics, Inc., Raritan, N.J.

[21] Appl. No.: 68,112

[22] Filed: Aug. 20, 1979

[51] Int. Cl.³ .............................................. B07C 5/342
[52] U.S. Cl. ................................... 209/3.1; 209/579;
209/906; 250/222 PC; 346/75; 356/72;
361/226; 364/413
[58] Field of Search ................................ 209/3.1–3.3,
209/571, 579, 906, 127 R; 250/222 R, 222 PC;
356/39, 72, 73, 335, 338; 361/226; 364/413;
346/75

[56] References Cited

U.S. PATENT DOCUMENTS

| | | | |
|---|---|---|---|
| 3,380,584 | 4/1968 | Fulwyler | 209/3 |
| 3,710,933 | 1/1973 | Fulwyler et al. | 209/3.1 |
| 3,761,941 | 9/1973 | Robertson | 346/1 |
| 3,769,627 | 10/1973 | Stone | 346/75 |
| 3,826,364 | 7/1974 | Bonner et al. | 209/3.1 |
| 3,836,912 | 9/1974 | Ghougasian et al. | 346/75 |
| 3,851,169 | 11/1974 | Faxvog | 250/222 |
| 3,878,519 | 4/1975 | Eaton | 346/1 |
| 3,907,429 | 9/1975 | Kuhn et al. | 356/28 |
| 3,920,702 | 10/1975 | Corll | 356/72 |
| 3,941,479 | 3/1976 | Whitehead | 356/102 |
| 3,953,860 | 4/1976 | Fujimoto et al. | 346/75 |
| 3,963,606 | 6/1976 | Hogg | 209/3 |
| 3,982,251 | 9/1976 | Hochberg | 346/1 |
| 4,025,926 | 5/1977 | Fujimoto et al. | 346/1 |
| 4,045,770 | 8/1977 | Arnold et al. | 346/75 |
| 4,047,183 | 9/1977 | Taub | 346/75 |
| 4,148,718 | 4/1979 | Fulwyler | 209/3.1 |

OTHER PUBLICATIONS

"Laser Flow Microphotometry for Rapid Analysis and Sorting of Mammalian Cells", Mullaney et al., Annals New York Academy of Sciences, vol. 267, pp. 176-190.
"Feedback for Synchronized Pressure Jet Using Optical Sensor", IBM Technical Disclosure Bulletin, vol. 16, No. 12, May 1974, pp. 3877-3878.
"Phase Detection on Ink Jet Droplets", IBM Technical Disclosure Bulletin, vol. 16, No. 3, Aug. 1973, p. 880.

Primary Examiner—Joseph J. Rolla
Attorney, Agent, or Firm—Audley A. Ciamporcero, Jr.

[57] ABSTRACT

A novel method and system are disclosed for detecting the breakpoint of a perturbed flow stream. The scattering and extinction of light caused by a perturbed stream at a preselected flow stream sensing point therealong is measured to produce a real time waveform proportional thereto. The real time waveform is differentiated to produce a differentiated waveform, which is then selectively monitored to distinguish a waveform exhibiting substantially three (positive and negative) peaks per cycle, whereby such detection indicates that at least a portion of the breakpoint region of said flow stream corresponds with said flow stream sensing point. In order to align the stream sensing point with respect to a preselected point within the breakpoint region of the flow stream, the breakpoint region of the stream is caused to move with respect to the stream sensing point until the breakpoint pulse width of one of the peaks corresponds with a preselected pulse width reference.

29 Claims, 12 Drawing Figures

SERVO SYSTEM TO CONTROL THE SPATIAL POSITION OF DROPLET FORMATION OF A FLUID JET IN A CELL SORTING APPARATUS

CROSS REFERENCE TO RELATED APPLICATIONS

The present application is related to the following applications, each of which is assigned to the assignee of the present application and are hereby incorporated by reference as if fully set forth herein: The invention of Igino Lombardo, Donald E. Barry, and W. Peter Hansen entitled, "Method For Detecting And Controlling Flow Rates Of The Droplet Forming Stream Of An Electrostatic Particle Sorting Apparatus", Ser. No. 68,231 filed Aug. 20, 1979; the invention of Igino Lombardo and W. Peter Hansen entitled, "Method And Apparatus For Positioning The Point Of Droplet Formation In The Jetting Fluid Of An Electrostatic Sorting Device", Ser. No. 68,113, filed Aug. 20, 1979; the invention of Igino Lombardo and Donald E. Barry entitled, "Automatic Relative Droplet Charging Time Delay System For An Electrostatic Particle Sorting System Using A Relatively Moveable Stream Surface Sensing System", Ser. No. 68,259, filed Aug. 20, 1979; the invention of Igino Lombardo and Donald E. Barry entitled, "Method For Automatically Setting The Correct Phase Of The Charge Pulses In An Electrostatic Flow Sorter", Ser. No. 68,234, filed Aug. 20, 1979; and the invention of Donald E. Barry and Igino Lombardo entitled, "A Method For Measuring The Velocity Of A Perturbed Jetting Fluid In An Electrostatic Particle Sorting System", Ser. No. 68,235, filed Aug. 20, 1979.

As to Ser. No. 68,235, please see generally pages 15-22; as to Ser. No. 68,113 see generally pages 15-24; as to Ser. No. 68,259, see generally pages 15-22; as to Ser. No. 68,234, see generally pages 15-21; and as to Ser. No. 68,231, see generally pages 15-25.

BACKGROUND OF THE INVENTION

The present invention relates generally to the field of electrostatic flow sorters, and more particularly to those sorters which are adapted to sense the presence and/or character of particles in a laminar flow stream and to slectively sort those particles by breaking that stream into a number of discrete droplets, and sorting those droplets containing such preselected particles. Such sorters are known for use in sorting and analyzing cellular compositions of given biological samples, as for example in the counting/analysis of cell types for a given blood sample.

In an apparatus of this general type, laminar flow is established through an area at which a light scattering, florescence or volume measurement is taken. Once a cell of interest has been sensed, and electronic time delay is normally activated for the length of time required for the cell to cover the distance from the point of cell detection to the point of droplet formation. Droplet formation may be accomplished by vibrating a flow chamber or orifice through which the stream passes, at a frequency sufficient to cause droplet formation, usually on the order of about 40,000 cycles per second. When a cell of interst arrives at the droplet formation point, a charging pulse may be applied to charge the droplet (plus, minus, or neutral) so that as the droplet of interest enters a subsequent DC field, it may be deflected as desired for collection. A general overview of this technique is provided in "Laser Flow Micrphotometry For Rapid Analysis And Sorting Of Mammalian Cells", Mullaney, et al, Annals New York Academy Of Sciences, Vol. 267, pages 176-190 (see in particular, pages 180 and FIGS. 3 and 4).

Such particle sorters are also disclosed in U.S. Pat. Nos. 3,710,933 (Fulwyler, et al) and 3,380,584 (Fulwyler) and 4,148,718 (Fulwyler). In these patents, sorting is accomplished in accordance with a selected paramter which may be size, volume, presence of radioactivity, color, florescence, light absorption or any quality capable of being translated into an electrical quantity. These patents additionally disclose single or multi parameter measurements to effect such sorting.

In order to selectively sort those droplets containing cells which are determined to be of particular interest, apparatus of this general type generally depends upon a flow rate estimate for the fluid containing a particular cell. This flow rate estimate is used to estimate the time between cell detection and the droplet breakpoint, at which selective charging of the droplet to be sorted takes place. As disclosed in U.S. Pat. No. 3,710,933, such systems are normally aligned and adjusted prior to taking cell measurements. In particular, droplet formation is normally checked by illuminating the emerging liquid jet near the flow chamber with a strobe light or equivalent light source. The strobe light is synchroflashed with respect to the oscillator frequency. Droplet formation can then be viewed using a microscope, and by varying the voltage and frequency applied to the stream perturbing transducer, droplet formation can be adjusted for a given nozzle diameter and flow rate. See U.S. Pat. No. 3,710,933, Column 11, lines 14-49.

As described particularly in U.S. Pat. No. 3,710,933, (Fulwyler, et al), by pressurizing various reservoirs with known pressures, flow rates can be estimated and cell flow rate adjusted by varying the relative pressures between the various reservoirs feeding into the flow stream. The approximate time delay between cell sensing and droplet formation (which is estimated in Fulwyler, et al to be in the order of 1400 microseconds) can be estimated so that an appropriate droplet charging generator will operate in combination with a pulse height analyzer and cell separation logic to charge the selected cell containing droplets for subsequent electrostatic sorting. p A number of factors affect the ability of a given apparatus to selectively sort one or more types of target cells from a continuous cell stream. Even assuming that the detection equipment for identifying each cell to be sorted is 100% accurate, differences in flow rate, temperature, fluid viscosity, and transducer performance can affect the time delay or location of the desired target-cell-containing droplets at the breakpoint, which is the point at which a charge pulse must be administered to insure that the target cell will be subsequently electrostatically sorted.

Heretofore, one of the methods used to adjust such a sorting apparatus involves running a test sample through that apparatus which is set or programmed to sort for one or more readily identifiable cell types. According to this procedure, the delay time is manually adjusted until those droplets which are sorted from the flow stream are found to contain the expected number of target cells. While this method, used alone or in combination with the stroboscopic method discussed above, has achieved some success in this art, it is prone to a certain degree of error, particularly during periods of extended machine use and/or changing operating conditions, such as changing sample viscosities and/or temperatures.

In U.S. Pat. No. 3,826,364 (Bonner, et al), a particle sorting method and apparatus are disclosed wherein a coaxial flow stream is released through a vibrating nozzle. Inspection (interrogation) of the stream by one or more cell sensing means for sensing cells in the stream occurs immediately downstream of the nozzle. In the Bonner, et al device, charging pulses are supplied at appropriate times for proper separation of the drops through the use of delay units which are adjusted to provide the necessary time delay to allow for travel time of the particle from the point of particle scatter detection to the point where the stream breaks into drops. Bonner states:

"With the present arrangement the delay time between observation of a particle and its capture by a separating droplet is predicatable to within three drop periods. Such high degree of predictability is due primarily to the uniform velocity of the inner particle containing stream 12A of the coaxial flow jet. That is, across the inner stream 12A the stream velocity is substantially uniform whereby particles anywhere within the cross-section of the inner stream travel with the same velocity from the point of observation to the drop separation point of the stream." U.S. Pat. No. 3,826,364, Col. 7, lines 22-32.

As further explained in the Bonner, et al disclosure, the duration as well as the time of application of the charging pulse is critical to the separation of at least the droplet containing the target particle to be sorted. After describing a preferred charging pulse which will charge at least three drops, Bonner, et al states:

"Obviously, if instrument tolerances, variations, drift and like permitted, then a drop charging time sufficient to charge only two successive drops, or a single drop, could be employed." U.S. Pat. No. 3,826,364, Col. 8, lines 2-6.

As also pointed out by Bonner, et al, a drop breaking from a given flow stream carries with it a charge which is proportional to the potential between the droplet stream and the surrounding electrodes or charging surfaces at the time the drop separates from the stream. If the drop breaks off from the jet stream during the transistion time from the drop charge pulse, either during the leading or trailing edge of that pulse, some intermediate value between zero and the desired full charge may be imparted to the target droplet. In the Bonner, et al apparatus, on/off transistions of the drop charging pulse are synchronized with the drop formation means, whereby charge pulse transitions may be synchronized to occur only intermediate the formation of droplets and not when droplets separate from the stream. This is made possible in the Bonner device by the provision of a variable phase control unit included in the transducer drive circuit which is adjusted for proper timing of droplet formation with the droplet charge pulse. As with the Fulwyler devices discussed above, stroboscopic illumination of the stream permits stream viewing through a suitable microscope, the stroboscopic illumination being synchronized by the drop charging pulses such that the stream, and more particularly the defleted drops, may be illuminated to ensure that the deflected drops contain the desired particles to be sorted.

More recently, various apparatus and method have been proposed for timing the application of a charge pulse so that droplets containing the particles to be sorted may be selectively charged. In U.S. Pat. No. 3,963,606 (Hogg), a particle separator is disclosed for separating particles in a fluid according to certain particle characteristics. The Hogg device includes a means for adjusting an electrical delay to be equal to the time between the emergence of a particle from a jet formng aperture to the point of break off. Hogg proposes the use of a movable scale in place of the ground glass of prior art projection microscopes, this scale being linked to a potentiometer of an RC oscillator to thereby control the oscillator's frequency. A second potentiometer for controlling the clock oscillator frequency is coupled to a height adjustment member of the aperture, this frequency being used to clock delay shift registers such that the charging pulse may easily be made to occur at the appropriate time, irrespective of fluctuations of pressure, velocity, amplitude and frequency of the droplet forming generator. See U.S. Pat. No. 3,963,606, (Hogg) Col. 2, lines 23-36. Accordingly, Hogg represents a more automated version of the stroboscopic projection microscopic technique discussed above.

Droplet forming characteristics in a perturbed stream have also been considered in connection with the art of ink jet printing. In the ink jet printing art, where discrete ink droplets formed in an ink jet stream are electrostatically directed to form characters on a recording surface, particular attention has been paid to establishing uniform droplet formation and charging characteristics. Since the charge imparted to any given droplet at its breakpoint is proportional to its surface area, i.e., the shape of that droplet at the breakpoint, and since even slight charge variations may produce erratic deflection characteristics, ink jet printing artisans have proposed various systems for producing an ink jet stream comprising uniformly shaped and uniformly charged droplets which will exhibit predictable down stream deflection behavior. These problems are complicated by the tendency of perturbed streams to form "satellites" which not only affect the charge imparted to preceeding or succeeding droplets, but also alter the volume of those droplets, thereby correspondingly affecting print uniformity.

In the ink jet printing art, numerous systems have been proposed for sensing the characteristics of a perturbed ink jet stream, either above or below the breakpoint of that stream. U.S. Pat. No. 3,907,429 (Kuhn, et al) discloses a method and device for detecting the velocity of droplets formed from a liquid stream. According to this disclosure, discrete droplets are directed between a pair of apertures and a light source which is strobed at a selected frequency and directed towards the apertures. By detecting the time between when a first of the apertures is blocked by a droplet in the stream as indicated by the light being broken during the strobe and the time when a second of the apertures is blocked by another droplet, when the light source is counted, the velocity of the droplets may be measured and a correction of the velocity made by changing the pressure of the manifolds supplying the liquid stream. In U.S. Pat. No. 3,769,627 (Stone) an ink jet printing system using ion charging of droplets is disclosed wheren a light source and photocell located downstream from the breakpoint of a perturbed stream is used to sense the passage of discrete droplets and to time delayed charges subsequently applied thereto. Stone states:

"Selective drop charging involves the induction of charges in the drop being formed by a surrounding charged electrode. The induced charge varies in accordance with the inducing voltage until the instant in time when the droplet physically separates from the stream. From that time on, the induced charged is trapped and remains with the drop. It is obvious, therefore, that the charging process must be carefully synchronized with the timing of the drop break off. This involves the use of complex phasing control sensors and loops. This in turn, increases the cost of the equipment.

It is an object of this invention to provide an ink drop charging system which does not depend upon the synchronization of the charging with the break off time.

It is another object of this invention to produce an ink drop charging system, which charges drops after they break off from the ink jet stream" U.S. Pat. No. 3,769,627 (Stone), Col. 1, lines 18–35.

This method is accomplished by using the above-described photocell arrangement for the purpose of counting and synchronizing charges applied as discrete droplets pass a plurality of separate charging stations which respond to coded information applied to each station in synchronism with the passage of each drop.

As disclosed in U.S. Pat. No. 4,047,183 (Taub), efforts have also been made to control the formation and shape of droplets in an ink jet stream by sensing the surface wave profile of the continuous portion of the stream (upstream from the breakpoint) by illuminating that portion of the stream with a radiant energy source such as a laser. The surface wave profile produced by illuminating the stream is sensed to provide the fundamental and harmonic frequency components thereof, and a perturbation drive signal, the amplitude and relative phase of which is a function of the sensed frequency components, is provided for controlling the formation and shape of the droplets. After discussing the advantages and difficulties of controlling the break off geometry, particularly with the respect to the illumination of satellite formations, Taub discloses the practical desirability of measuring the ink jet stream upstream rather than downstream from the droplet break off point:

"The ideal time to sense the frequency, phase, and amplitude components of the ink jet stream for determining drop break off characteristics is at the precise time droplets are formed therefrom. This is usually impossible to achieve, however, since the droplets are normally formed inside the charged electrode. Therefore, according to the present invention, the drop break off characteristics are determined by sensing upstream of break off, rather than downstream as taught by the prior art. The continuous portion, that is, the portion just prior to break off of the stream is sensed to determine the break off characteristics. In response to the sensed characteristics, a piezoelectric drive signal is provided which controls droplet formation, and accordingly provides increased drop charging efficiency." U.S. Pat. No. 4,047,143 (Taub), Col. 4, lines 53–68.

Taub discloses a system wherein an ink jet manifold having a perturbation means such as a piezoelectric crystal emits a perturbed ink jet stream into charge electrode structures which are pulsed in "a well known manner" to selectively apply charge to the droplets. A source of radiant energy, which may comprise a helium-neon laser, emits radiant energy focused on the continuous portion of the jet "just prior to the jet entering the charged electrode structure". "Since the ink is opaque, a shadow is formed" which is imaged through a lens onto a substrate which has a slit formed therein. The shadow formed thereby represents the surface wave profile of the jet which is a representation of the respective amplitudes and relative phase of fundamental and harmonic frequencies. Taub states:

"The light passing through the slit 44 is influenced by the wave passing a given point on the perimeter of the jet, and accordingly is a representation of the frequency components of the jet at this particular point, as well as being indicative of the shape of a given droplet when it breaks-off downstream. It is necessary to make this slit somewhat larger than the largest diameter to be measured, typically the drop diameter, so that the clipping of the wave form does not occur, as well as preventing the generation of spurious diffraction effects. A narrow band pass filter 48, which has a band pass on the order of 100 A centered in the laser wavelength, is used so measurements may be made in room light. The light passed by the filter 48 is then transmitted to a photomultiplier tube 50 which measures the intensity of the light. Therefore, the output voltage of the photomultiplier tube 50 is proportional to the diameter of the jet blocking the slit, which is to say, to the local diameter of the jet at the point being probed . . . It is to be appreciated that the signal output . . . may be applied to analyzing means 80 by other timing means such as a stepping motor, or alternatively may be applied concurrently to inputs of devices 82, 84 and 86, rather than in the time sequence described." U.S. Pat. No. 4,047,183. See Col. 6, lines 27–68, Col. 7, lines 1–26.

In Taub's preferred embodiment, the output signal so obtained is conditioned to control the fundamental and harmonic frequencies applied to the piezoelectric perturbation means for controlling the droplet formation and shape of droplets produced by the ink jet stream.

For other disclosures of ink jet printing systems using optical sensors, see IBM Technical Disclosure Bulletin Volume 16, No. 12, May 1974, Page 3877-8, entitled "Feedback For Synchronized Pressure Jet Using Optical Sensor"; and IBM Technical Disclosure Bulletin, Vol. 16, No. 3, August 1973, Page 880, entitled "Phase Detection on Ink Jet Droplets".

For other disclosures relating to various ink jet printing synchronization systems, please refer to U.S. Pat. No. 4,025,926 (Fujimoto, et al) entitled, "Phase Synchronization For Ink Jet System Printer"; U.S. Pat. No. 4,045,770 (Arnold, et al) entitled, "Method and Apparatus For Adjusting The Velocity Of Ink Drops In An Ink Jet Printer"; U.S. Pat. No. 3,953,860 (Fujimoto, et al) entitled, "Charge Amplitude Detection For Ink Jet System Printer"; U.S. Pat. No. 3,761,941 (Robertson) entitled, "Phase Control For A Drop Generating and Charging System"; U.S. Pat. No. 3,836,912 (Ghougasian, et al) entitled, "Drop Charge Sensing Apparatus For Ink Jet Printing System"; U.S. Pat. No. 3,982,251 (Hochberg) entitled, "Method and Apparatus For Recording Information On a Recording Medium"; U.S. Pat. No. 3,878,519 (Eaton) entitled, "Method and Apparatus For Synchronizing Droplet Formation In A Liquid Stream".

For other patents disclosing particle or flow sorting systems, please see U.S. Pat. No. 3,941,479 (Whitehead) entitled, "Use Of Modulated Stimulus To Improve Detection Sensitivity For Signals From Particles In A Flow Chamber"; U.S. Pat. No. 3,851,169 (Faxvog) entitled, "Apparatus For Measuring Aerosol Particles"; and U.S. Pat. No. 3,910,702 (Corll) entitled, "Apparatus For Detecting Particles Employing Apertured Light Emitting Device".

SUMMARY OF THE INVENTION

The present invention comprises a novel system and method for detecting the breakpoint of a perturbed flow stream. The scattering and extinction of light caused by a perturbed stream at a preselected flow stream sensing point is measured to produce a real time wave form proportional thereto. By differentiating the real time wave form to produce a differentiated wave form, it is possible to selectively monitor the differentiated wave form to determine whether the stream sensing point is located within the breakpoint region. The detection of substantially three peaks per cycle, a first positive peak followed by two negative peaks, provides that indication. In the event that the stream sensing point is not located to correspond with the breakpoint region, the flow stream breakpoint is moved relative to the stream sensing point by one of several methods, the preferred method being to vary the amplitude of perturbation of the stream at least until detection of the breakpoint region occurs. Alternatively, the flow rate, perturbation frequency, or location of the flow stream sensing point may be varied in order to establish correspondence between the flow stream sensing point and the breakpoint region of the perturbed stream.

Monitoring of the differentiated wave form is preferably accomplished by monitoring selected, alternate cycles to count the positive and negative peaks thereof. In order to desensitize the system to spurious noise, threshold peak levels are preferably established so that only positive and negative peaks exceeding preselected thresholds will be counted. In the event that the stream sensing point is determined to be within the breakpoint region, precise alignment of the stream sensing point with respect to a particular portion of the breakpoint region may be effected by comparing the pulse width of the first negative peak of the differentiated wave form to a pulse width reference value which will produce a proportional error signal for slightly varying the position of the breakpoint with respect to the stream sensing point, to establish a preselected alignment therebetween.

In the event that the stream sensing point does not correspond with the breakpoint region, the breakpoint region is caused to sweep relative to the stream sensing point at least until the breakpoint region is detected as corresponding with the stream sensing point. In order to prevent such sweeping from occuring prematurely as the result of spurious noise peaks, etc., such sweeping should not occur until a successive number, such as five, cycles have been monitored which indicate that the stream sensing point in fact does not correspond with the breakpoint region.

The present invention also provides a novel automated system for performing the preferred embodiment method of the present invention.

Accordingly, a primary object of the present invention is the provision of a novel method and system for detecting the breakpoint region of a perturbed fluid flow stream, and for controlling the location of the breakpoint of the stream with respect to a preselected stream sensing point. This and other objects of the present invention will become apparent from the following more detailed description.

BRIEF DESCRIPTION OF THE DRAWINGS

FIG. 2 is a graph of voltage waveforms present in the system of FIG. 1, the top voltage waveform (1A) representing the signal produced by the pin diode detector amplified by the detector amplifier, and the bottom waveform signal 1B representing the output signal of the inverting buffer;

DETAILED DESCRIPTION OF THE INVENTION

Although specific forms of the invention have been selected for illustration in the drawings, and the following description is drawn in specific terms for the purpose of not intended to limit the scope of the invention which is defined in the appended claims.

The present invention is intended for use particularly with electrostatic particle or flow sorting systems, and more particularly such systems which are intended to analyze and sort biological cells. Typically, a population of cells to be analyzed and sorted may be prepared (possibly by a dying process) and placed in a suitable solution that will act as a vehicle. That cell/sample solution, pressurized, is forced into a laminar flow through a narrow courts channel by another pressurized surrounding sheath fluid. At the correct sample/sheath pressure combination the cells will flow down the center of the channel in single file. At some point along the channel the cells are interrogated (usually by optical means) shortly before they are expelled through an orifice into free air flight, while still contained with the sample/sheath fluid. A quartz flow channel (and orifice) is mechanically coupled to a wall of an energized piezoelectric transducer which supplies the ultrasonic perturbation motion required for the controlled formation of droplets in the expelled fluid jet. Disturbances caused by the motion of the orifice force the fluid jet to break into droplets in a controlled fashion. The region where the jet seperates into droplets will be referred to as the breakpoint region, the precise breakpoint being that point in the perturbed flow stream where the seperation of droplets from the stream actually occurs.

As droplets are formed they may contain cells which are desired for isolation from other of the cells which have been interrogated. In this case, at precisely the correct time after detection, an electrostatic charge is applied to the stream just before the droplets containing the cell of interest seperates from the jet. The charge may be a variable length, positive, negative or zero in polarity. These droplets now charged, fall through a strong electric field and are deflected into their proper collection vials.

In order for a given cell to be sorted, the time for each cell to travel from the point of detection (interrogation) to the breakpoint must be precise and predictable. The time of travel, however, is a function of the fluid velocity in which the cell is suspended, and the spacial position of the breakpoint. If both of these conditions are met then the impending droplet will be properly charged and deflected, carrying with it the wanted cell. The time delay between a wanted or target cell and the time of droplet charging is displacement and velocity dependent, where the displacement is the distance between the point of detection (interrogation) and the point of impending droplet separation, and where the velocity is the velocity of the cell. Assuming that cell velocity is constant, proper charging and deflection of droplets depends on keeping the time delay and breakpoint position constant. If one or the other varies, a situation may occur where uncontrolled deflection or spraying of droplets makes collection difficult. The time delay of the charging pulse is percisely controlled electronically and can be considered constant. In practice, most problems are caused by shifts in breakpoint position. The position of the breakpoint (for a given orifice diameter and fluid velocity) is affected by the amplitude of the applied disturbance. The efficiency of the mechanical coupling between the orifice and the piezoelectric transducer, the surface tension and density of the fluid, and the relationship between the droplet spacing and the jet diameter. Since the amplitude of the transducer is easily varied, it may be used to actively shift at the breakpoint position. These relationships are described more fully in connection with the inventions set forth in the above references related patent applications, each of which are incorporated herein by reference.

Figure 1:
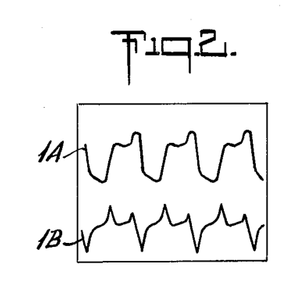
FIGS. 1(a) and 1(b) are a block diagram of the preferred embodiment system of the present invention.
Figure 1A:
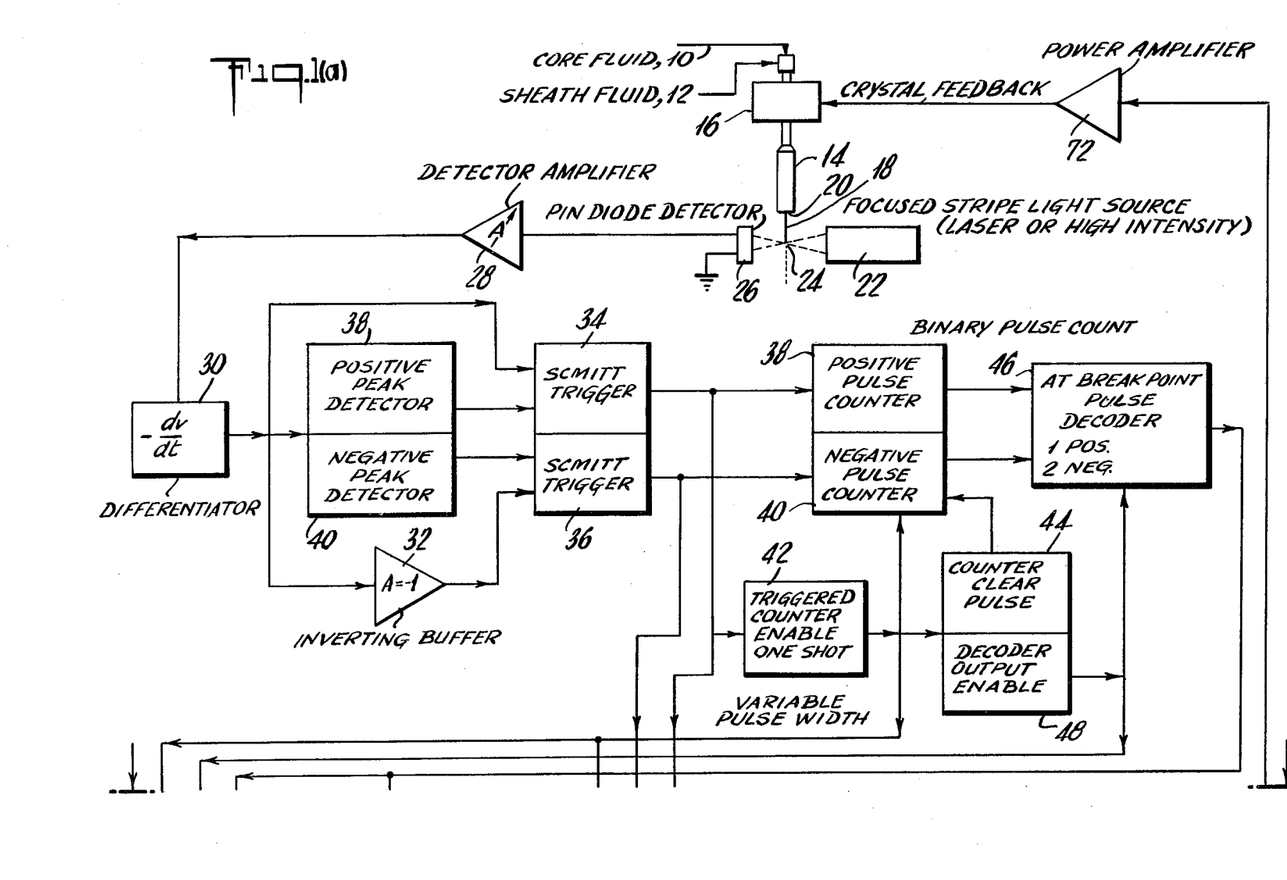
Figure 1B:
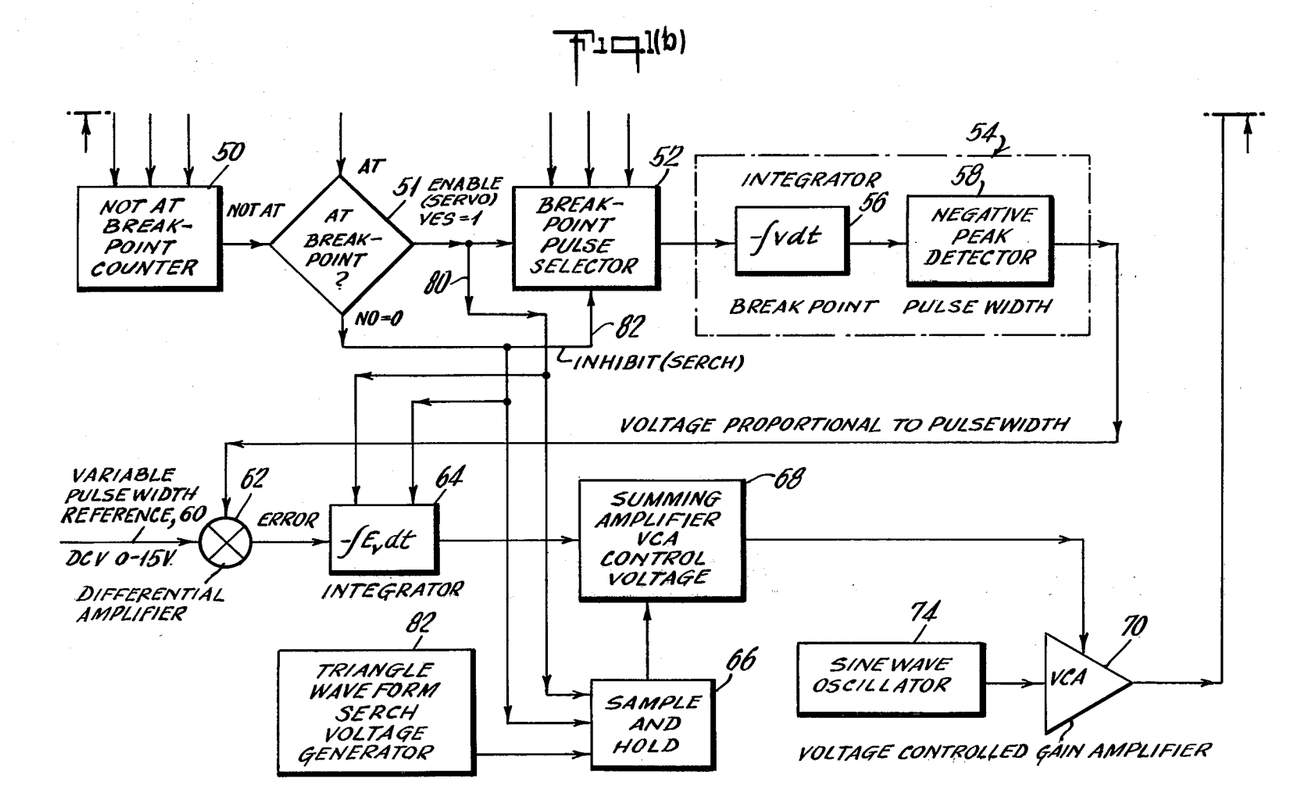

The present invention provides a novel system and method for sensing, controlling and aligning the breakpoint of a perturbed laminar flow stream to accomplish the purposes and results described above. Referring now to the figures and more particularly to FIG. 1, the sources of core fluid 10 and sheath fluid 12, as described above, are seen to be combined for travel through a quartz flow chamber 14 which is coupled to a piezoelectric transducer 16 for perturbing the laminar flow stream 18 upon exiting from the orifice 20 of the quartz flow channel. Within the quartz flow chamber 14 the laminar flow stream is interrogated for the purpose of detecting the presence of target cells which are to be sorted at the breakpoint of the laminar flow stream 18. A focused strip light source which is a laser or high intensity light source 22 is focused through a stream sensing point 24 on a pin diode detector 26. In the preferred embodiment of the present invention the laser or high intensity light source may be focused using an FC-200 Ortho Instruments lens assembly. This preferred optics comprises two cylindrical lenses which are 90° off rotational axis. Alignment of the cylindrical lenses with respect to the center of the axis of the laser is preferred for optimum focusing of the band, however the advantage of a wider tolerance in the horizontal plane for focusing is preferred because of stream wandering.

The output of the pin diode detector 26 is proportional to the degree of light scattering and extinction caused by the shape of the stream at the stream sensing point 24. The output from the pin diode detector is amplified by a detector amplifier 28 which produces an output signal illustrated as waveform 1A shown in FIG. 2, this output signal preferrably having approximately three volts peak-to-peak. Experiments have been conducted to determine the particular waveforms which will be produced by the pin diode detector depending upon the particular stream sensing point 24 and its relative location to the breakpoint of the laminar flow stream 18.

Figure 3:
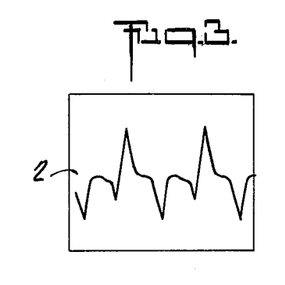
FIG. 3 is a voltage waveform of the input 4B and output 2 of the positive peak detector of the system illustrated in FIG. 1.
Figure 4:
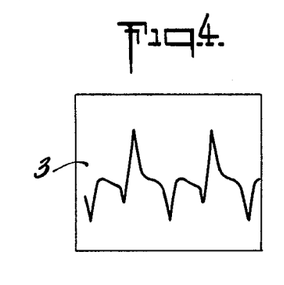
FIG. 4 is a voltage waveform for the negative peak detector showing the input 4B and output 3 of that detector.
Figure 5:
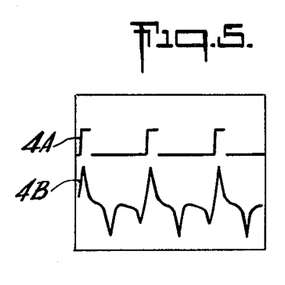
FIG. 5 shows voltage waveforms for signals 4A and 4B as indicated for the system illustrated in FIG. 1, the top trace (4A) of which represents the positive peak Scmitt trigger TTL output signal juxtaposed over the differentiated waveform 4B.
Figure 6:
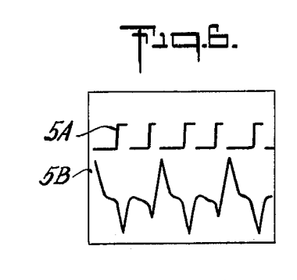
FIG. 6 is a voltage waveform for signals 5A and 5B as indicated for the system illustrated in FIG. 1, the top trace 5A being the waveform for the TTL output signal from the negative peak Scmitt trigger juxtaposed over the differentiated waveform 5B which is the output of the system differentiator.
Figure 7:
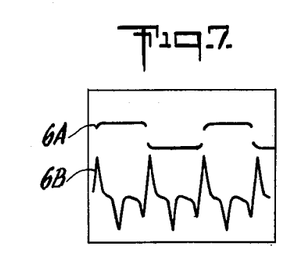
FIG. 7 shows the voltage waveform for signals 6A and 6B as indicated for the system illustrated in FIG. 1, signal 6A being the output signal generated by a variable pulse width one shot which is triggered on the leading edge of every other positive pulse, as seen by the juxtaposition of this waveform over the differentiated waveform signal 6B.

Varification of the waveform relationship to drop formation has been accomplished by displaying the light pulses from an LED strobe (which relates to what the human eye sees at any given time) with the pin diode detector output voltage. This varification procedure (with the use of a neutral density filter) permits the observation of the band of laser light and where it intersects the stream. It has been determined that by differentiating the output of detector amplifier 28, the precise nature of waveform 1A illustrated in FIG. 2 can more easily be determined by counting the number of positive and negative peaks per cycle. For example, when the stream sensing point is located below the breakpoint, the differentiated output signal contains one positive and one negative peak per cycle for distinct droplets, two positive and two negative peaks for a distinct droplet plus a distinct satelite, etc. When the stream sensing point is located above the breakpoint region, two peaks one positive and one negative per cycle, are observed in the differentiated waveform output. When, and only when, the laser is focused in the breakpoint region will three major peaks, one positive and two negative, occur per cycle. Accordingly, in the system illustrated in FIG. 1, a differentiator 30 is provided for inverting and differentiating signal 1A shown in FIG. 2 to create the differentiated signal waveform 4B shown in FIG. 5. Similarly, a true derivative signal, signal 1B in FIG. 2, may be produced by inverting buffer 32 for introduction into variable threshold Scmitt triggers 34 and 36, as described hereinafter. The differentiated output signal waveform 4B shown in FIG. 5 is utilized as the input to positive peak detectors 38 and 40, which detect the maximum value of the positive and negative peaks, respectfully, as shown for output signals 2 and 3 of FIGS. 3 and 4 respectfully. Outputs 2 and 3 are then used to set the thresholds of Scmitt triggers 34 and 36 at some preselected percentage of the detected peaks. This assures that only the wanted peaks will generate pulses even if the amplitude of signal 4B changes. The use of inverting buffer 32 permits Scmitt trigger 36 to "see" the negative peaks of the differentiated waveform as positive for counting purposes. The output of the Scmitt triggers 34 and 36, waveforms 4A and 4B of FIGS. 5 and 6 respectfully, are TTL output signals which are fed into respective positive pulse counter 38 and negative pulse counter 40, which are gated by signal 6A shown in FIG. 7 to count every other cycle. Signal 6A is generated by a variable pulse width one shot 42 which is triggered on the leading edge of every other pulse (signal 4A shown in FIG. 5). The no count periods are used for servo time and counter clearing, the latter of which is accomplished by counter clear pulse logic 44.

The outputs of the positive and negative pulse counters are fed into a decoder 46 whose output goes to a logic "0" when one positive and two negative pulses have been counted at the end of the count cycle. The output of the decoder is enabled by a "display" pulse from the decoder output enable one shot 48. The positive and negative pulse counters are then cleared for the next count cycles by counter clearing pulse logic 44, which is triggered by the falling edge of the decoder output enable pulse.

As described above, the system has now determined whether the stream sensing point corresponds to the breakpoint region of the perturbed flow stream by having determined whether or not one positive and two negative pulses occur in the differentiated output waveform. If at this point it is determined with some reliability that the stream sensing point is not at the breakpoint, the system of the present invention will begin to sweep the amplitude of the piezoelectric transducer drive voltage for the purpose of varying the breakpoint through a preselected range of locations. If, on the other hand, it is determined that the stream sensing point is within the breakpoint region, a servo system will be actuated for the purpose of precisely aligning the stream sensing point at a preselected position with respect to the breakpoint region. Accordingly, a decision must now be made based on the state of the decoder 46 output whether to servo (on the pulsewidth of the first negative pulse) or to sweep through the breakpoint control range. If the decoder 46 outputs a logic "0" during the period of the decoder enable 46 pulse, the system will servo on the pulse width of the first negative pulse in the cycle.

However, because of stream noise (particles in suspension or instantaneous shape variations) a means of desensitizing the decision flip-flop 51 is preferred. Accordingly, a not at breakpoint counter 50 is provided which counts in five cycle increments and goes to a logic "0" only when it receives five consecutive "not at breakpoint" pulses, that is, when the decoder output 46 is high during the decoder output enable 48 pulse. This eliminates the possibility of extraneous noise putting the system into the search mode.

Figure 8:
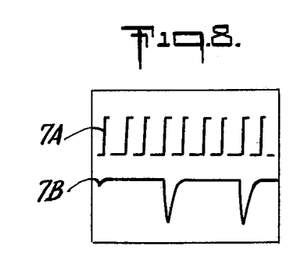
FIG. 8 shows a voltage waveform for signals 7A and 7B as indicated for the system as illustrated in FIG. 1 wherein first negative pulses (7A) isolated by the breakpoint pulse selector circuit are integrated to produce signal (7B)
Figure 9:
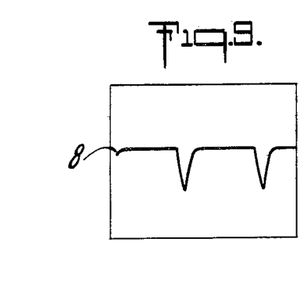
FIG. 9 shows the voltage waveform input 7B and output 8 of the negative peak detector.
Figure 11:
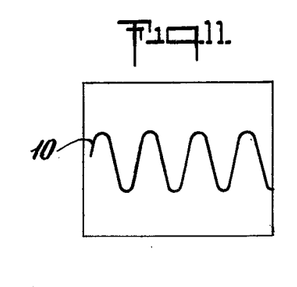
FIG. 11 shows a sinusoidal voltage waveform which is the output signal (10) of the sinewave oscillator indicated in FIG. 1.

Assuming that the optical source/sensor pair is focused on the breakpoint region, that is, that the steam sensing point corresponds to the breakpoint region such that the decoder 46 output is "0", the decision will be made to remain in the sevo mode. In this mode, the first negative pulse is isolated by a breakpoint pulse selector circuit 52. The breakpoint pulse selector circuit is enabled by the servo/search line 80, 82 which is shown as two separate lines in the block diagram. From here, the TTL level pulse will be integrated by the breakpoint pulse width unit 54 illustrated in dotted outline in FIg. 1. The breakpoint pulse width unit comprises an integrator 56 and negative peak detector 58. Since the output of the Scmitt trigger 36 is a positive pulse which is isolated by breakpoint pulse selector 52 (waveform 7A of FIG. 8). The TTL level pulse 7A is then integrated to produce signal 7B shown in FIG. 8, which integration causes an inversion of the signal, as shown in FIg. 8. A negative peak detector 58 then detects the negative peak (see waveform 8 illustrated in FIG. 9) to produce an output voltage which is essentially proportional to the input pulse width. Applicants have experimentally determined that variations in this pulse width value are proportionally related to the displacement of the stream sensing point from the desired alignment position of the stream sensing point with respect to the breakpoint region. Accordingly, output signal 8, which is a DC voltage level, is then compared to a pulse width reference voltage 60 by a differential amplifier 62. The resulting error voltage, which reflects the difference between the desired and actual pulse width, is fed into an integrator 64 that is also enabled by the servo/search line (an analog switch across the integrating capacitor 80, 82). The output from the error voltage integrator is now summed with the last DC level seen by the sample and hold circuit 66, which will be described more fully hereinafter. The resulting voltage from this summing amplifier 68 controls the gain of a voltage controlled amplifier (VCA) 70. The input voltage to the VCA is a sinusoid whose amplitude is one volt peak to peak (see signal 10 illustrated in FIG. 11) and whose frequency is set depending on the particular diameter of the orifice 20. Accordingly, a sinewave oscillator 74 is provided for producing signal 10. The gain of the VCA can vary between 0 and 10 with a $-15$ to 0 volt swing on the control bias input. The output of the VCA is then further amplified by a power amplifier 72 to supply drive power to the transducer 16. While the system is in the servo mode, feedback continues until the error voltage is reduced to 0.

Figure 10:
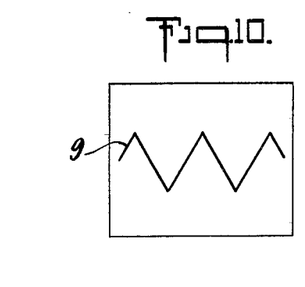
FIG. 10 shows a voltage waveform for the signal (9) produced by the triangular waveform search generator illustrated in FIG. 1.

As mentioned above, when the circuit loses its lock on the breakpoint region waveform, the system automatically goes into a search mode. The search mode is activated after five consecutive count cycles when the output of the decoder 46 is high, thereby causing the output of the not at breakpoint counter 50 to go to a logic "0". This forces the servo/search line 80, 82 into the search state. In this mode, both the breakpoint pulse selector 52 and the error voltage integrator 64 are turned off and the sample and hold circuit 66 which samples the triangular search voltage (signal 9 illustrated in FIG. 10) to be switched to the sample state. A triangular waveform search voltage generator 82 is accordingly provided for producing signal 9, which triangular sweep voltage signal is summed by the summing amplifier 68, which continues to sum the error voltage integrator output of integrator 64, which is now 0. The summing amplifier drives the control bias input of the VCA 70 with the resultant voltage. The transducer drive voltage, now modulated by a low frequency triangular wave, causes the breakpoint to move throughout its total control range. Once the breakpoint is found, the system switches back into the servo mode. The normal sorting sequence of the particle sorter is halted at any time the system loses lock on the breakpoint waveform. An external counter will tally the number of times the system searches the control range after the breakpoint has been lost and, if greater than a preset value, an indicator will alert the operator that the breakpoint is out of the control range and that corrective procedures should be carried out to rectify the condition. Such procedures may include orifice cleaning or fluidic system back flushing.

As seen from the above, a novel method and system are provided for automatically detecting, establishing and aligning the breakpoint of a perturbed laminar flow stream with respect to a preselected stream sensing point. The system and method of the present invention are extremely economical, and will prove to substantially increase the reliability and accuracy of electrostatic particle sorters of this general type.

It will be understood that various changes in the details, materials and arrangement of parts which have been herein described and illustrated in order to explain the nature of this invention may be made by those skilled in the art within the principle and scope of the invention as expressed in the following claims. As used herein, "perturbed" or "perturbation" is meant to include not only mechanical/vibratory methods for creating discontinuities in the stream, but also discontinuities which are induced by other means such as alteration of stream surface tension, for example, by electrical, thermal, or optical means. Likewise, periodic or aperiodic perturbations are meant to be included.

It will further be understood that the "Abstract of the Disclosure" set forth above is intended to provide a non-legal technical statement of the contents of the disclosure in compliance with the Rules of Practice of the U.S. Patent and Trademark Office, and is not intended to limit the scope of the invention described and claimed herein.

What is claimed is:

1. A method of detecting at least the breakpoint region of a perturbed flow stream, comprising:
   (a) measuring at least the scattering of light caused by said perturbed stream at a preselected flow stream sensing point therealong to produce a real time waveform proportional thereto;
   (b) differentiating said real time waveform to produce a differentiated waveform;
   (c) selectively monitoring said differentiated waveform to distinguish a waveform exhibiting substantially three, positive and negative peaks per cycle, whereby detection of said three peaks per cycle indicates that said breakpoint region of said flow stream corresponds with said flow stream sensing point.

2. The method of claim 1 comprising the additional step of moving said flow stream sensing point relative to said stream to locate said breakpoint region.

3. The method of claim 1 wherein step (c) further comprises the step of distinguishing per cycle, a first peak of a given polarity and two successive peaks of opposite polarity.

4. The method of claim 1 wherein step (c) comprises the steps of establishing threshold positive and negative peak-amplitude valves at preselected proportions of the expected values of said three peaks to be monitored, and counting the number of such peaks per cycle which exceed such threshold values to detect said breakpoint region.

5. The method of claim 1 wherein the step of measuring at least the scattering of light caused by a perturbed stream further comprises the step of measuring the extinction of light caused by said perturbed stream.

6. The method of claim 1 comprising the additional step of selectively varying the flow rate of said flow stream at least until said breakpoint region is caused to correspond with said preselected flow stream sensing point.

7. The invention of claim 6 wherein said method comprises the additional step of serially monitoring a plurality of cycles of said differentiated waveform for inhibiting the step of selectively varying the flow rate of said flow stream at least until a serial plurality of said cycles do not exhibit said three, positive and negative peaks per cycle, whereupon the step of selectively varying the flow rate of said flow stream is permitted to take place.

8. The method of claim 1 wherein step (c) comprises the step of monitoring selected cycles of said differentiated waveform.

9. The method of claim 8 wherein said monitoring step comprises monitoring alternate ones of said cycles.

10. The method of claim 1 wherein said method comprises the further step of precisely aligning said stream sensing point relative to a preselected portion of said breakpoint region.

11. The invention of claim 10 wherein said step of precisely aligning comprises the steps of altering the breakpoint of said stream until at least one of said peaks meets a preselected reference peak parameter.

12. The method of claim 1 comprising the additional step of selectively varying the perturbation of said flow stream at least until said breakpoint region is caused to correspond with said preselected flow stream sensing point.

13. The method of claim 12 wherein said step of selectively varying the perturbation comprises selectively varying the frequency of said perturbation.

14. The method of claim 12 comprising the additional step of monitoring a plurality of cycles of said differentiated waveform to inhibit said selective varying of the perturbation of said flow stream at least until a plurality of such cycles do not exhibit said three peaks per cycle, whereupon said selected varying of said perturbation of said flow stream is permitted to take place.

15. The method of claim 12 wherein said step of selectively varying the perturbation comprises selectively varying the amplitude of said perturbation.

16. The method of claim 15 wherein said selective varying of said amplitude comprises sweeping said amplitude through a predetermined range at least until said breakpoint region is detected.

17. An apparatus for detecting the breakpoint of a perturbed flow stream, comprising:
   (a) stream sensing means for measuring at least the scattering of light caused by said perturbed stream at a preselected flow stream sensing point therealong to produce a real time waveform proportional thereto;
   (b) analysis means for differentiating said real time waveform to produce a differentiated waveform; and
   (c) breakpoint location means for selectively monitoring said differentiated waveform to distinguish a waveform exhibiting substantially three, positive and negative peaks per cycle, whereby detection of said three peaks per cycle indicates that said breakpoint region of said flow stream corresponds with said flow stream sensing point.

18. The invention of claim 17 wherein said apparatus additionally comprises shift means for moving said flow stream sensing point relative to said stream to locate said breakpoint region.

19. The invention of claim 17 wherein said apparatus further comprises flow rate adjustment means for selectively varying the flow rate of said flow stream at least until said breakpoint region is caused to correspond with said flow stream sensing point.

20. The apparatus of claim 17 wherein said breakpoint location means further comprises peak identification means for distinguishing per cycle a first peak of a given polarity and two successive peaks of opposite polarity.

21. The invention of claim 17 wherein said breakpoint location means further comprises threshold means for establishing threshold positive and negative peak-amplitude values at preselected proportions of the expected values of the three peaks to be monitored, and counting means for counting the number of such peaks per cycle which exceeds such threshold values, to detect said breakpoint region.

22. The invention of claim 17 wherein said breakpoint location means further comprises breakpoint monitoring means for monitoring selected cycles of said differentiated waveform.

23. The invention of claim 22 wherein said breakpoint monitoring means further comprises alternate breakpoint waveform monitoring means for monitoring alternate ones of said cycles.

24. The invention of claim 17 wherein said apparatus further comprises stream sensing point alignment means for precisely aligning said stream sensing point relative to a preselected portion of said breakpoint region.

25. The invention of claim 24 wherein said breakpoint alignment means comprises servo means for altering the breakpoint of said stream until at least one of said peaks meets a preselected reference peak parameter.

26. The invention of claim 17 wherein said apparatus further comprises perturbation means for selectively varying the perturbation of said flow stream at least until said breakpoint region is caused to correspond with said preselected flow stream sensing point.

27. The invention of claim 26 wherein said perturbation means further comprises frequency adjustment means for selectively varying the frequency of said perturbation.

28. The invention of claim 26 wherein said perturbation means further comprises amplitude adjustment means for selectively varying the amplitude of said perturbation.

29. The invention of claim 28 wherein said amplitude adjustment means comprises amplitude sweep means for sweeping said amplitude through a predetermined range at least until said breakpoint region is detected.

* * * * *